United States Patent
Purves

[11] 3,996,788
[45] Dec. 14, 1976

[54] FLOW RESISTANCE APPARATUS AND METHOD FOR ASSEMBLED ACOUSTIC PANELS

[75] Inventor: Robert Byron Purves, Renton, Wash.

[73] Assignee: The Boeing Company, Seattle, Wash.

[22] Filed: Aug. 6, 1975

[21] Appl. No.: 602,494

[52] U.S. Cl. .................................. 73/38; 73/159
[51] Int. Cl.² ...................................... G01N 15/08
[58] Field of Search .............. 73/38, 37, 37.7, 159, 73/40

[56] References Cited
UNITED STATES PATENTS

| 2,706,904 | 4/1955 | Hertel | 73/38 |
| 3,056,281 | 10/1962 | Smyth | 73/38 |
| 3,466,925 | 9/1969 | Ziegenhagen et al. | 73/38 |

*Primary Examiner*—S. Clement Swisher
*Assistant Examiner*—Joseph W. Roskos
*Attorney, Agent, or Firm*—Morris A. Case

[57] ABSTRACT

A puck to contact an acoustic panel has open-ended compartments to flow air through then back through the face sheet of an acoustic panel while measuring the air pressure difference across the face sheet.

12 Claims, 8 Drawing Figures

U.S. Patent  Dec. 14, 1976  Sheet 1 of 2  3,996,788
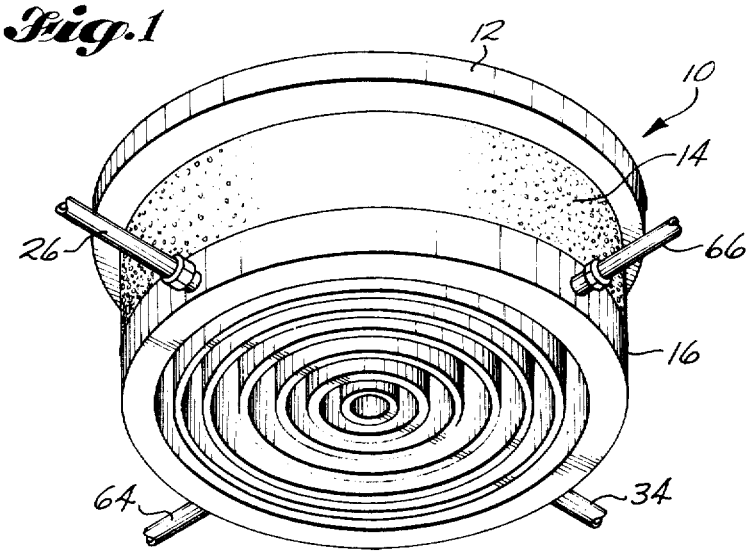
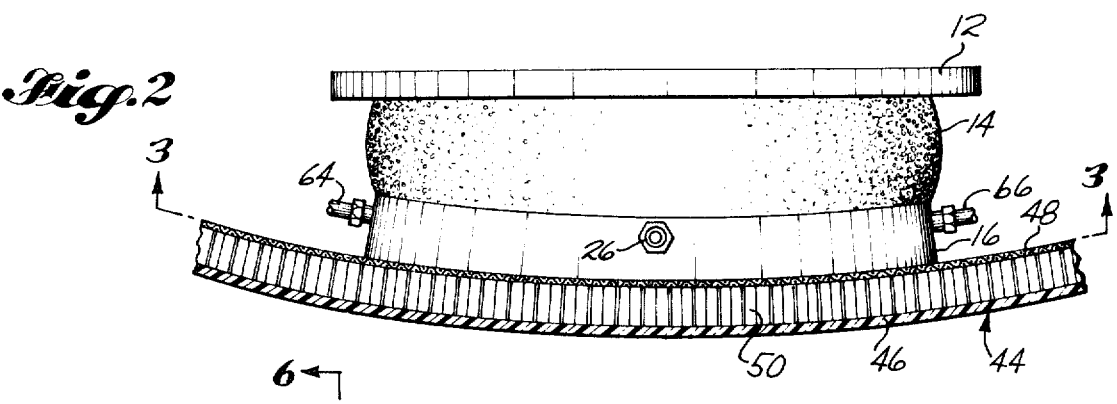
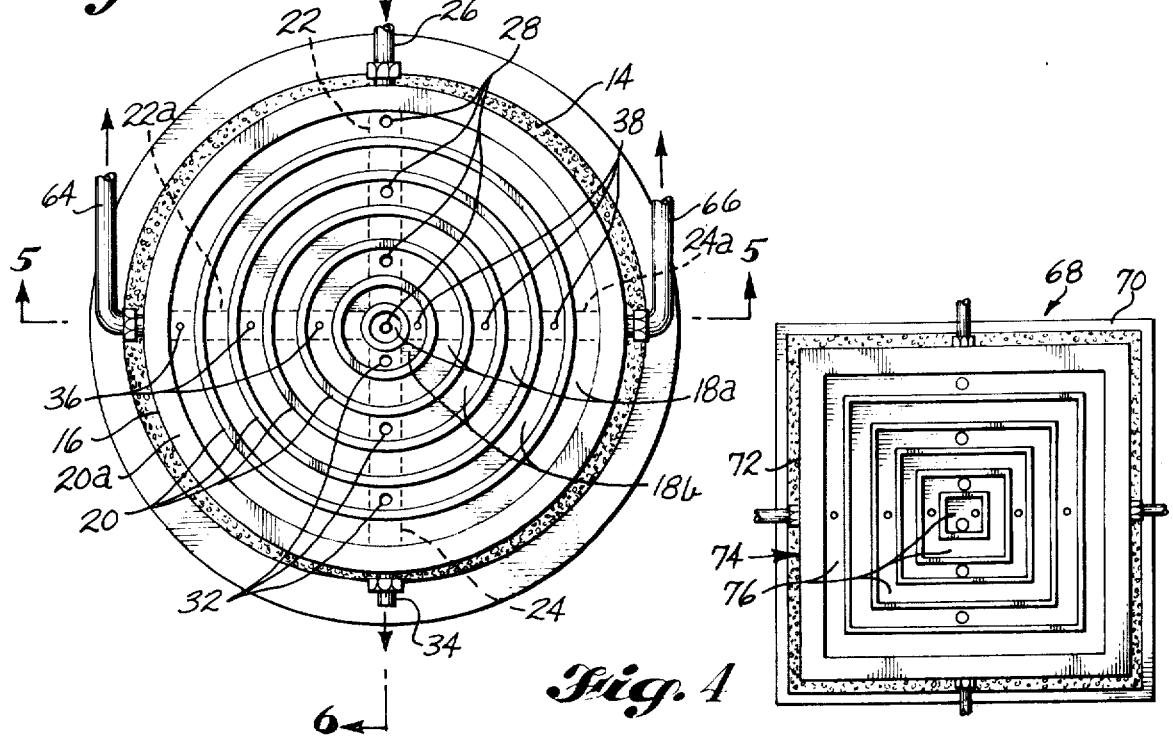

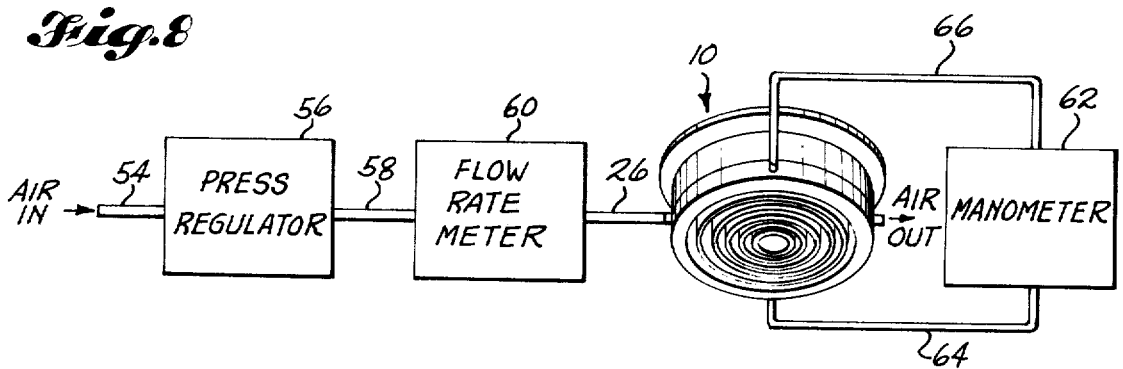
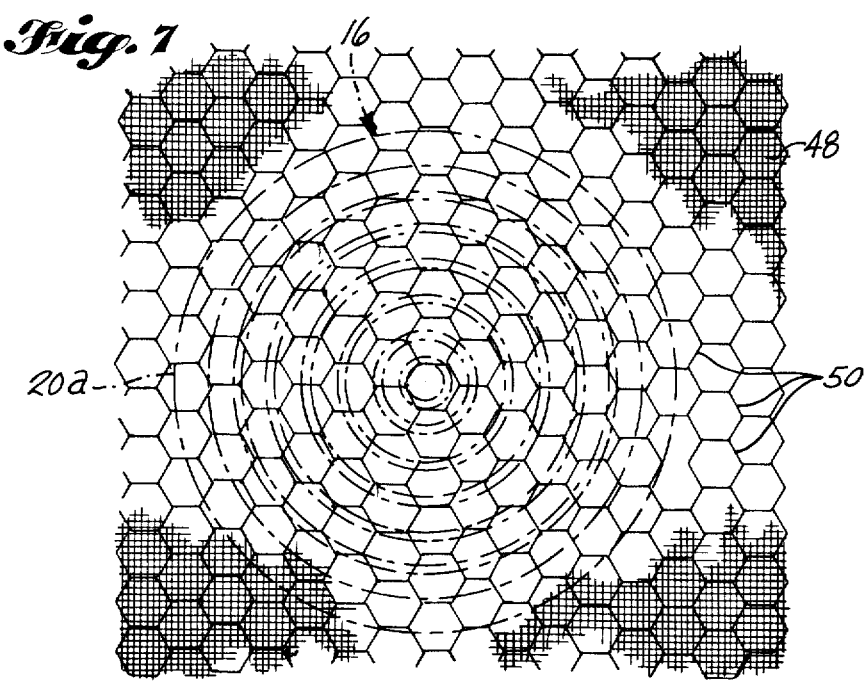
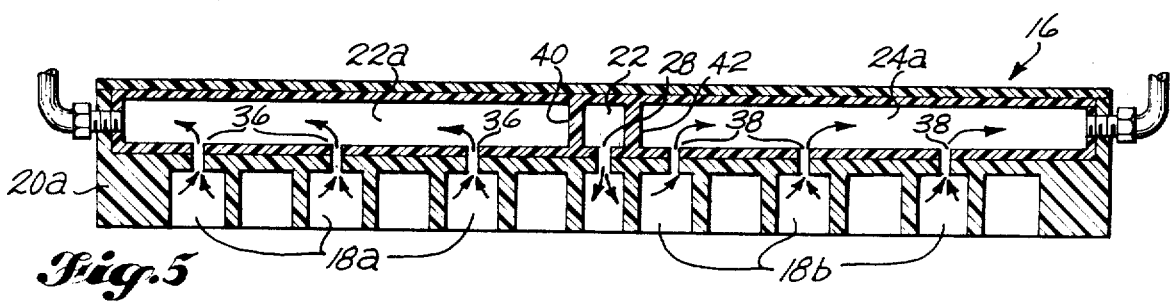
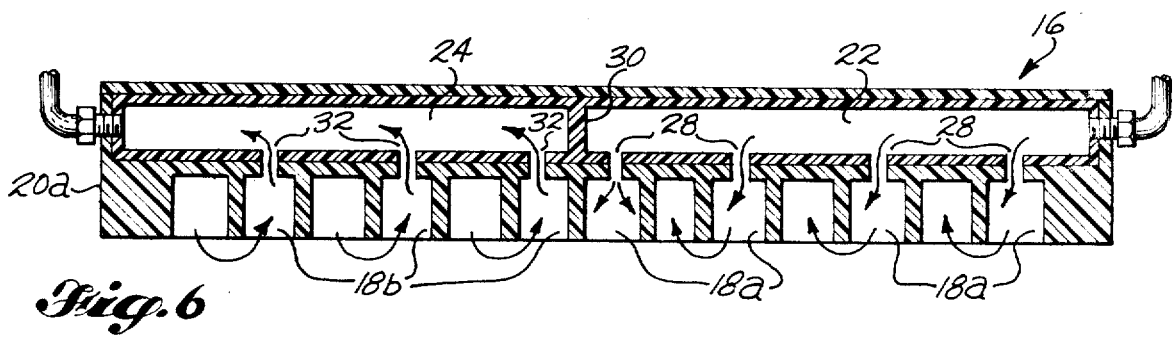

FLOW RESISTANCE APPARATUS AND METHOD FOR ASSEMBLED ACOUSTIC PANELS

BACKGROUND OF THE INVENTION

In an acoustic panel of the Helmholtz resonator type, the panel has a solid hard backing plate, a series of chambers, usually of honeycomb material, and a porous face sheet. The porosity of the face sheet is selected according to the desired sound dampening required. The porous face sheet may be effected in production by the process of building up the face sheet, by the method of adhering the face sheet to the chambers, and by painting. In use the porous areas may become filled with particles. It is known to check the porosity of the face sheet by blowing air at a constant rate through the face sheet while measuring the pressure drop between the incident and the exhausting air. Using this method, the flow resistance of the face sheet is determined from the particle velocity and the pressure drop. Unfortunately, this method may not be used to test a completed Helmholtz panel. The panel may only be tested without the solid backing plate. Thus, the face sheet must either be tested in an intermediate step in production before the backing sheet or plate is in place or a coupon must be prepared along with a production part. The backing sheet is then removed from the coupon before determining the porosity as found by measuring the flow resistance of the face sheet. A completed panel may only be tested by the destruction method of removing the backing plate.

It was found that a completed acoustic panel, including a panel that has been used, may be tested with the use of a special puck or head.

SUMMARY OF THE INVENTION

A puck for contacting a face sheet has a series of open-ended compartments with the open ends extending toward the face sheet. Alternate compartments communicate with a chamber or header in the puck. Intermediate compartments communicate with a second chamber or header in the puck. A regulated flow of air passes from alternate compartments in the puck through interstices in the face sheet into open cells of the honeycomb core material in the panel thence back up through the face sheet into the intermediate compartments in the puck. the compartments are sized to permit air from a compartment to enter the cells of the honeycomb core and return from the cells through an adjacent compartment. Thus, the width of a compartment plus an adjacent separating member is less than the width of an individual cell. The air may enter the puck under pressure or it may be pulled by a vacuum.

An assembled acoustic panel is tested by passing a regulated flow of air, through the face sheet, into and out of the interior of the panel and registering the pressure differential between the air pressure before and after passing through the face sheet.

It is an object of this invention to provide means for non-destructive testing of a completed Helmholtz resonator acoustical panel.

It is another object of this invention to provide for non-destructive testing of an in use Helmholtz resonator acoustical panel.

DESCRIPTION OF THE DRAWINGS

FIG. 1 is a perspective view of the puck of this invention.

FIG. 2 shows a side elevational view of the puck of FIG. 1 in contact with a Helmholtz resonator acoustical panel.

FIG. 3 shows a plan view taken along lines 3 — 3 of FIG. 2.

FIG. 4 shows an alternate embodiment of the puck of FIG. 3.

FIG. 5 is a sectional view showing only the housing part of the puck with the section taken along lines 5 — 5 of FIG. 3.

FIG. 6 is a sectional view taken along lines 6 — 6 of FIG. 3, and showing only the housing part of the puck.

FIG. 7 shows a view taken along lines 7 — 7 of FIG. 3, and showing only the part of the puck that contacts the face sheet of the acoustic panel.

FIG. 8 shows a schematic of the device of this invention.

DETAILED DESCRIPTION

A puck or head 10 has a backing plate 12, a resilient cushion 14, preferably of a soft foam rubber or foamed plastic and a housing 16, which is preferably flexible. The housing as best shown in FIGS. 3, 5 and 6 has a series of open-ended compartments 18 with alternating compartments 18a, and intermediate compartments 18b, and with all compartments separated by resilient walls 20. The housing in this embodiment has four chambers or headers 22, 22a, and 24 and 24a for distributing air between compartments. In this embodiment, header 22 receives air under pressure through line 26, and distributes it to openended compartments 18a through a series of orifices 28, each of which leads from the header to a compartment. Headers 22 and 24 are separated from each other by wall 30. Header 24 has a series of openings 32 for communicating between the header and open-ended compartments 18b. In operation compressed air from header 22 and compartments 18a returns through compartments 18b through header 24 and then is vented through line 34. A series of holes 36 communicate between alternating compartments 18a and header 22a, and another series of holes 38 communicate between intermediate compartments 18b and header 24a. Holes 36 and 38 leading into headers for communication with the manometer are preferably smaller than air directing holes 28 and 32. Header 22 is separated from header 22a by wall 40, and from header 24a by wall 42.

In FIG. 2 an acoustical panel 44 is shown which has a solid backing plate 46, a porous face sheet 48, and a honeycomb core 50. The panel as shown here is curved, but may have compound curves and the puck 10 will still intimately contact the contour of the face sheet. Pressure is applied to the backing plate 12 of the puck and there is sufficient elasticity in the cushioning material 14 and flexibility and resilience in the housing 16 to flex to match the shape of the panel. The open-ended compartments 18 are directed away from the puck backing plate 12 so that the ends 52 of the walls 20 of the compartments contact the face sheet 48 of the panel 44 to form a seal between the wall ends of the puck and the panel face sheet. The compartment width is dimensioned with respect to the individual cells of the honeycomb core, as best shown in FIG. 7, to permit air to enter a honeycomb cell from one compartment and return from the cell to an adjacent compartment. Thus, the width of a compartment plus the width of an adjacent compartment wall is less than the width of a honeycomb cell in the core. The outermost wall 20a, however, is wider than a cell width to cover the cells and prevent outward flow of air from the outermost compartment.

The schematic of FIG. 8 shows the apparatus required to test a completely assembled acoustic panel. Air from a compressor, not shown, passes through line 54 into a pressure regulator 56 prior to passing the air through line 58 into a flow rate meter 60 thence into line 26 leading into the puck. In this embodiment a manometer 62 is used to record the differential pressure in the puck between the air pressure before passing through the face sheet 48 and the air pressure after passing through the face sheet. Line 64 extends from the manometer to chamber 22a of the housing to indicate the pressure before, and line 66 extends from the manometer to chamber 24a to indicate the air pressure after passing through the face sheet.

In operation the puck 10 is pressed against the face sheet 48 of the acoustic panel 44 and held in intimate contact. Air pressure and the rate of air flow into the puck is set as required for the face sheet being tested. The air at a controlled pressure and velocity is then passed through line 26 and into header 22 where it is distributed to alternating open-ended compartments 18a. The air passes through the face sheet into cells 50 of the honeycomb core then back from the cells passing again through the face sheet into intermediate open-ended compartments 18b. The air is collected from these compartments into header 24 and out to atmosphere through line 34. Air pressure in the alternating compartments, which is the pressure before passing through the face sheet, is recorded by being collected in header or chamber 22a, and passing through line 64 to connect to one side of manometer 62. At the same time the air pressure in the intermediate compartments, which is after the air has twice passed through the face sheets, is recorded by being collected in header 24a, passing through line 66 to connect to the opposite side of the manometer. Knowing the rate of flow of the air through the face sheet and the pressure drop of the air through the face sheet, the open area can be checked. In a Helmholtz resonator acoustic panel, the desired flow resistance through the face sheet can be determined from knowledge of the various dimensions of the panel and the sound dampening desired. This flow resistance is normally expressed in Rayl units. The Rayl value using the device of this invention may be expressed as $R = \Delta P/Q\ S;$ where R=Rayl value, $\Delta P$ is the pressure differential across the face sheet, Q is volume flow rate, and S is the area of the surface through which air is flowing. Thus, it can readily be seen that when one knows the desired flow resistance or Rayl value, one can check this value in an assembled panel by the device of this invention.

It is obvious that other configurations of the puck of this invention may be used without departing from its scope. For example in the embodiment shown in FIG. 4 the puck 68 has backing plate 70, resilient cushion 72 and a housing 74 which has rectangular shaped compartments 76. The headers and the air distribution in the housing is similar to that shown in the embodiment of FIGS. 3; 5, and 6. However, it is understood that in any embodiment additional headers with openings for communication with the compartments may be used for distributing the air throughout the puck.

What is claimed is:

1. A device for measuring flow resistance through a permeable face sheet of a panel having a permeable face sheet, a solid sheet and a honeycomb core between the sheets wherein the device comprises: a puck to contact a permeable face sheet, said puck having compartments separated by resilient members having a width of compartment plus resilient member less than a cell width of a honeycomb core; means for introducing a regulated flow of gas to alternate compartments; means for removing the gas from intermediate compartments; and means for measuring difference in gas pressure between alternate and intermediate compartments.

2. A device as in claim 1 wherein the compartments are circular in shape.

3. A device as in claim 1 wherein the compartments are rectangular in shape.

4. A device as in claim 1 wherein the puck further comprises: means for cushioning to allow the puck to intimately contact a contoured face sheet.

5. A device for checking interstices in a face sheet of an acoustic panel of the type having a porous face sheet, a solid backing sheet and a honeycomb core therebetween, the device comprising: a puck compartmented and having the compartments open to a surface for contacting a porous face sheet of an acoustic panel, means for introducing air into alternate compartments, means for removing air from intermediate compartments, means for measuring pressure differential between alternate and intermediate compartments, and the compartments are of a width to permit air to enter a cell in the honeycomb core of the acoustic panel from a compartment in the puck and to permit the air to leave the cell through an adjacent compartment.

6. A device as in claim 5 wherein the compartments are circular in shape.

7. A device as in claim 5 wherein the compartments are rectangular in shape.

8. A device as in claim 5 wherein walls between the compartments are resilient.

9. A device as in claim 8 further comprising means for adapting the puck to permit intimate contact between the puck and a contoured panel.

10. A head for a device for checking interstices in a face sheet of a panel having a honeycomb core and a backing sheet comprising: a backing plate to permit introduction of force to bring a contacting surface of the head in intimate contact with a porous face sheet of a panel; a resilient material adjacent the backing plate; a flexible housing adjacent the resilient material, said housing comprising: a series of compartments open ended in a direction away from the backing plate, each of said compartments in combination with one adjacent separating member having a width less than a cell width of the honeycomb core, a first chamber communicating with alternate compartments, a second chamer communicating with intermediate compartments, means for allowing the introduction of a regulated flow of air to the first chamber, and means for allowing the air to escape from the second chamber.

11. A method of directly checking the interstices in a porous face sheet in an acoustical panel having a honeycomb core and a backing sheet, the steps comprising: contacting a face sheet with a puck, passing air at a regulated rate from the puck through the face sheet into open cells of the honeycomb core and back to the puck through the face sheet, and registering pressure differential of the air in the puck before and after passing through the face sheet.

12. A method of checking an acoustical panel having a porous face sheet, a solid backing sheet and a honeycomb core, the steps comprising: utilizing a compartmented puck; placing the puck against a porous face sheet of an acoustic panel; passing air, at a regulated rate, from compartments in the puck through the face sheet, into honeycomb core cells, back from the cells through the face sheet and out different compartments in the puck; and registering the difference in pressure in the puck before and after passing through the face sheet.

* * * * *